United States Patent
Nellis

(10) Patent No.: US 11,351,079 B2
(45) Date of Patent: Jun. 7, 2022

(54) VAPORIZER CONTAINMENT TENT

(71) Applicant: Donald Nellis, Newburgh, IN (US)

(72) Inventor: Donald Nellis, Newburgh, IN (US)

( * ) Notice: Subject to any disclaimer, the term of this patent is extended or adjusted under 35 U.S.C. 154(b) by 64 days.

(21) Appl. No.: 16/783,284

(22) Filed: Feb. 6, 2020

(65) Prior Publication Data

US 2020/0297566 A1 Sep. 24, 2020

Related U.S. Application Data

(60) Provisional application No. 62/822,395, filed on Mar. 22, 2019.

(51) Int. Cl.
| | |
|---|---|
| *A61G 10/02* | (2006.01) |
| *A61M 11/04* | (2006.01) |
| *E04H 15/38* | (2006.01) |
| *E04H 15/64* | (2006.01) |
| *E04H 15/16* | (2006.01) |

(52) U.S. Cl.
CPC .......... *A61G 10/02* (2013.01); *A61M 11/041* (2013.01); *E04H 15/16* (2013.01); *E04H 15/38* (2013.01); *E04H 15/64* (2013.01)

(58) Field of Classification Search
CPC ...... A61G 10/02; A61M 11/041; E04H 15/16; E04H 15/38; E04H 15/64
See application file for complete search history.

(56) References Cited

U.S. PATENT DOCUMENTS

| | | | | |
|---|---|---|---|---|
| 2,190,613 | A * | 2/1940 | Sittler | A61G 10/04 128/205.26 |
| 2,503,725 | A * | 4/1950 | Greene | A61G 10/04 128/205.26 |
| 2,508,050 | A * | 5/1950 | Valente | A61G 10/04 128/205.26 |
| 2,699,775 | A * | 1/1955 | Cameto | A61G 10/04 128/205.26 |
| 2,915,074 | A * | 12/1959 | Cameto | A61G 10/04 52/2.21 |
| 3,878,570 | A | 4/1975 | Donnelly | |
| 4,285,355 | A * | 8/1981 | Lundblade | E04H 15/42 135/147 |
| 4,885,000 | A | 12/1989 | Hogan | |
| 4,949,714 | A * | 8/1990 | Orr | A61G 10/04 128/200.24 |
| 5,832,919 | A * | 11/1998 | Kano | A61G 10/005 128/205.26 |
| 6,210,320 | B1 * | 4/2001 | Rogone | A61G 11/00 600/21 |
| 6,367,476 | B1 * | 4/2002 | Conn | A61G 10/04 128/205.26 |

(Continued)

Primary Examiner — Kendra D Carter
Assistant Examiner — Jonathan S Paciorek
(74) Attorney, Agent, or Firm — Boudwin Intellectual Property; Daniel Boudwin

(57) ABSTRACT

A vaporizer containment tent. The vaporizer containment tent includes a housing. The housing defines an interior volume that has an open lower end. The housing also defines a first end opposite of a second end, with an elongated area therebetween. A cut out is placed on the second end of the housing, corresponding to an area where the feet of an individual using the vaporizer containment tent would extend. The housing also includes a flap that is placed on the side portion of the housing.

19 Claims, 2 Drawing Sheets

(56) References Cited

U.S. PATENT DOCUMENTS

| | | | | |
|---|---|---|---|---|
| 6,500,111 | B1* | 12/2002 | Salmon | A61G 11/00 |
| | | | | 600/22 |
| 7,322,315 | B2* | 1/2008 | Brewer | A01K 1/033 |
| | | | | 119/474 |
| 8,256,044 | B1* | 9/2012 | Park | A47C 29/006 |
| | | | | 135/117 |
| 2005/0236026 | A1 | 10/2005 | Anticoli et al. | |
| 2016/0074268 | A1 | 3/2016 | Breegi et al. | |

* cited by examiner

VAPORIZER CONTAINMENT TENT

CROSS REFERENCE TO RELATED APPLICATIONS

This application claims the benefit of U.S. Provisional Application No. 62/822,395 filed on Mar. 22, 2019. The above identified patent application is herein incorporated by reference in its entirety to provide continuity of disclosure.

BACKGROUND OF THE INVENTION

The present invention relates to a vaporizer containment tent. More specifically, the present invention relates to an apparatus to provide a confined, personal area for an individual to more effectively breath in vapors that are created by a vaporizer or other similar device.

Many respiratory ailments, such as chest congestion, sinus congestion and the like create discomfort and frustration for many individuals. Particularly, infants and young children that suffer from respiratory ailments will be unable, or struggle to, breathe and to clear their lungs. In addition to being uncomfortable, these ailments can create difficult breathing conditions, prolonging treatment time.

Respiratory ailments are commonly treated using vaporizers, humidifiers or other similar devices. These devices utilize steam or cool water vapors to clear up congestion by dissipating hem throughout a confined area that the patient is located in. Generally, the more effectively the vapors are contained, the more effective that treatment by vaporizers is. Keeping these vapors contained, however, can be difficult. This is particularly true in larger areas, such as a bedroom. Therefore, there is a defined need amongst the known arts for an apparatus that provides convenience to a user by allowing for the more effective and efficient containment of vapors produced by a vaporizer, or similar device.

SUMMARY OF THE INVENTION

In view of the foregoing disadvantages inherent in the known types of peripheral vaporizer accessories now present in the prior art, the present invention provides a vaporizer containment tent wherein the same can be utilized for providing convenience for the user when subjecting an individual to vapor treatment using a vaporizer.

The present system comprises a housing. The housing defines an interior volume that has an open lower end. The housing also defines a first end opposite of a second end, with an elongated area therebetween. A cut out placed on the second end of the housing, corresponding to an area where the feet of an individual using the vaporizer containment tent would extend. The housing also includes a flap that is placed on the side portion of the housing. The flap allows for access to the interior volume of the housing. In some embodiments, the housing further includes at least one vent, so that when a vaporizer creates vapors in the interior volume of the housing, the vapors will be able to escape through the vent or vents.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
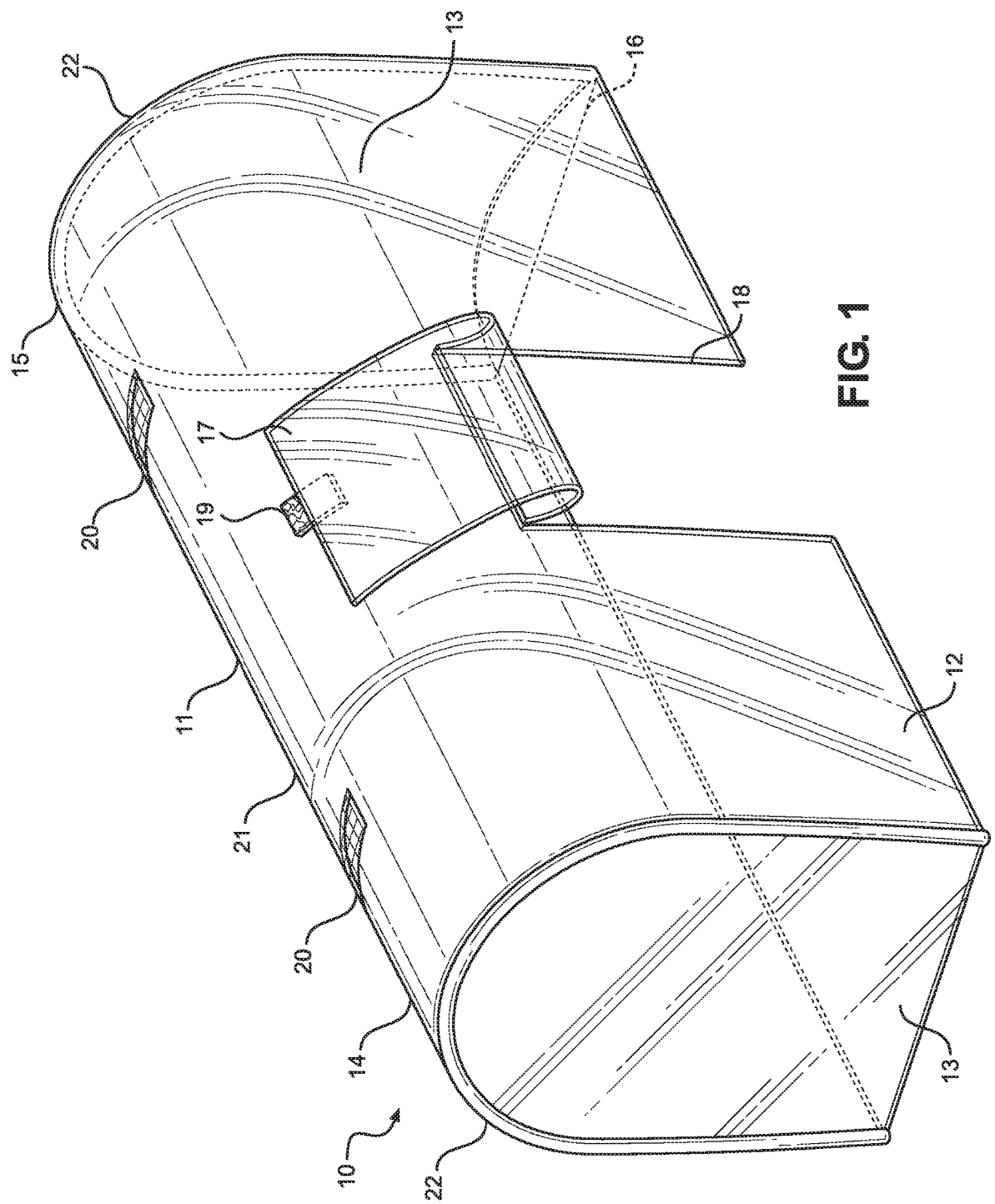
FIG. 1 shows a perspective view of an embodiment of the vaporizer containment tent.

Reference is made herein to the attached drawings. Like reference numerals are used throughout the drawings to depict like or similar elements of the vaporizer containment tent. The figures are intended for representative purposes only and should not be considered to be limiting in any respect.

Referring now to FIG. 1, there is shown a perspective view of an embodiment of the vaporizer containment tent. The vaporizer containment tent 10 comprises a housing 11. The housing 11 comprises an open lower end 12. As such, an individual placed upon a horizontal surface may have the vaporizer containment tent 10 placed over the top of him or her. In the illustrated embodiment, the housing 11 is hemicylindrical and is defined by a pair of semicircular side walls 13. The housing 11 is elongated, such that a first end 14 is defined oppositely of a second end 15. The housing 11 is shaped such that it covers a rectangular area. In other embodiments, the housing 11 is of an alternative shape. The housing 11 can be dimensioned to allow one of a targeted class of individuals to enhance the treatment of a vaporizer or similar device. For example, the housing 11 may be dimensioned for use by infants, for use by children or for use by adults.

In some embodiments, the housing 11 also comprises a cut out 16. The cut out 16 is disposed on a bottom end of the second end 15 of the housing 11. In the illustrated embodiment, the cut out 16 is arcuate, or otherwise bowed, in configuration. The cut out 16 is dimensioned to allow an individual placed in the housing 11 to extend his or her feet through the cut out 16. As such, the individual in the housing 11 will not become uncomfortably warm, as they would have access to cooler air outside of the housing 11 through the cut out 16. Additionally, a caretaker for an infant or otherwise dependent individual may utilize the cut out 16 to ensure that the individual is responsive while they are in the housing 11 by peering through the cut out 16 or examining the individual's feet as they are extended through the cut out 16.

The housing 11 further comprises a flap 17. The flap 17 is disposed on a side portion of the housing 11. The flap 17 is movable between an open configuration (demonstrated in FIG. 1) and a closed configuration (demonstrated in FIG. 2). The open configuration is defined where an opening 18 in the housing 11 is formed. The opening 18 provides access to the interior cavity defined by the housing 11. The opening 18 is dimensioned to receive a vaporizer, or similar device, therethrough, such that an individual may place, move or otherwise manipulate the vaporizer, or similar device, via the opening 18. The closed configuration (demonstrated in FIG. 2) is defined where the opening 18 is covered by the flap 17. In the illustrated embodiment, the fastener 19 is configured to affix the flap 17 to the housing 11, thereby holding the flap 17 in an open configuration. As such, the fastener 19 can maintain the open configuration without an individual having to manually hold the flap 17 in an open configuration. In the illustrated embodiment, the fastener 19 is a hook and loop fastener wherein the hook and loop fasteners are disposed on a bottom end of the flap 17 and a central point of the side portion of the housing 11. As such, the fastener 19 may be easily and effectively engaged and disengaged by an individual.

In the illustrated embodiment, the housing 11 further comprises at least one vent 20. The at least one vent 20 is disposed on an upper end 21 of the housing 11. The at least one vent 20 is configured to allow excess steam, moisture or humidity generated by the vaporizer, or similar device, to escape from the housing 11. Being placed in a vertically elevated position, the at least one vent 20 is configured to allow for warm, rising air to escape from the housing 11. As such, convenience is provided to the individual as the humidity in the interior cavity of the housing 11 will not exceed a certain level. In the illustrated embodiment, a pair of vents 20 are provided. The pair of vents 20 comprises a first vent placed proximally to the first end 14 of the housing 11 and a second vent proximally disposed to the second end 15 of the housing 11.

In construction, the illustrated embodiment comprises a pair of rigid members 22 configured to define the shape of the housing 11. The pair of rigid members 22 provide structural support to the vaporizer containment tent 10. The pair of rigid members 22 may be adjustable in length and shape. As such, the shape and the height of the housing 11 itself is adjustable. The pair of rigid members 22 are identical in size and shape, such that the housing 11 is of a consistent shape and size throughout the entire length thereof.

Figure 2:
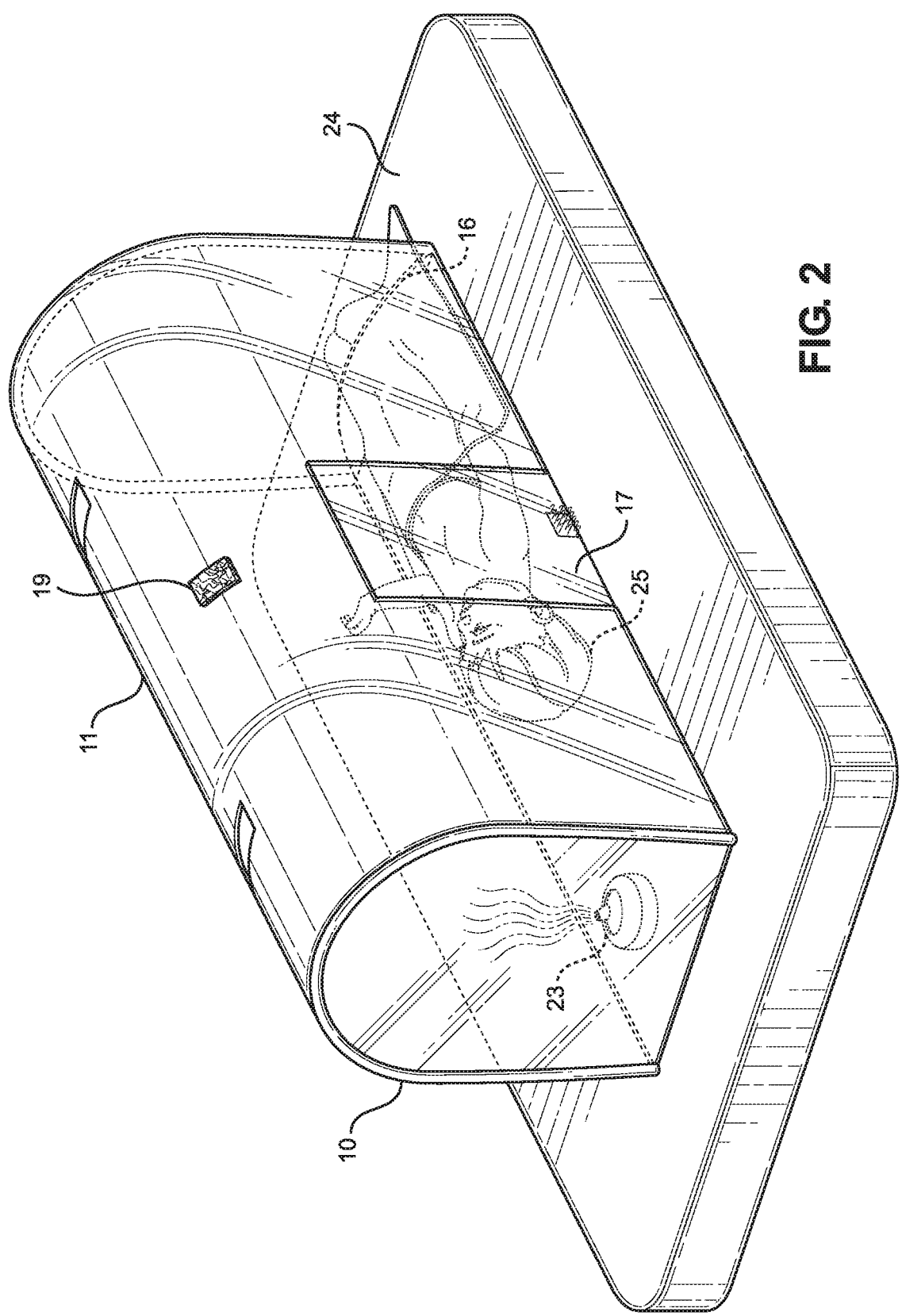
FIG. 2 shows a perspective view of an embodiment of the vaporizer containment tent in use.

Referring now to FIG. 2, there is shown a perspective view of an embodiment of the vaporizer containment tent in use. The housing 11 is made of a non-absorbent material, such that when a vaporizer 23 or similar device is placed in the housing 11, the moisture and steam generated by the vaporizer 23 will not be absorbed by the material of the housing 11. As such, the risk of the material of the housing 11 or becoming infested with mold or mildew s reduced. Additionally, in some embodiments, the housing 11 is constructed of lightweight materials, such that the housing 11 is easy for an individual to move and set up. For example, the housing 11 can be made of a rubberized fabric material, such as rubberized canvas, or a similar material like vinyl.

In use, the vaporizer containment tent 10 is placed upon a horizontal surface, such as a mattress 24. The vaporizer containment tent 10 may be dimensioned for specific use in a targeted apparatus, such as a crib. The vaporizer containment tent 10 is placed upon the mattress 24 over top of the vaporizer 23 and an individual 25 to be treated using the vaporizer 23. In the case of a larger vaporizer 23, the vaporizer 23 may be placed on the outside peripheral area of the vaporizer containment tent 10, such that the vapor produced thereby may enter the vaporizer containment tent 10 through the flap 17. In the illustrated embodiment, the feet of the individual 25 are extended through the cut out 16 of the housing 11. Furthermore, as shown, the flap 17 is placed in the closed configuration. As such, the vapors generated by the vaporizer 23 are more effectively contained within the housing 11, allowing the individual 25 inside of the housing 11 to breathe in the vapors more effectively.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A vaporizer containment tent, comprising:
   a housing defining an interior volume with an open lower end;
   the housing having a first end disposed opposite a second end;
   a cut out disposed on a bottom end of a side wall of the second end of the housing;
   wherein the cut out is arcuate in shape and extends entirely across the bottom end of the sidewall of the second end of the housing;
   a flap disposed on a side portion of the housing between the first end of the housing and the second end of the housing;
   the flap in operable connection with the open lower end of the housing.

2. The vaporizer containment tent of claim 1, further comprising at least one vent disposed on an upper end of the housing.

3. The vaporizer containment tent of claim 1, wherein the flap comprises a fastener, the fastener configured to hold the flap in an open configuration.

4. The vaporizer containment tent of claim 3, wherein the fastener is a hook and loop fastener.

5. The vaporizer containment tent of claim 1, wherein the housing is composed of a rubberized fabric material.

6. The vaporizer containment tent of claim 1, wherein the housing is composed of a vinyl material.

7. The vaporizer containment tent of claim 1, wherein the housing is hemicylindrical in shape.

8. The vaporizer containment tent of claim 1, wherein a frame of the housing comprises a pair of rigid members configured to define the shape of the housing therebetween.

9. The vaporizer containment tent of claim 8, wherein the pair of rigid members are adjustable.

10. A vaporizer containment tent, comprising:
    a pair of rigid members placed such that a housing is formed therebetween;
    wherein the pair of rigid members are of an inverted U-shape;
    wherein a curved side wall is defined between the pair of rigid members;
    the housing defining a first end opposite a second end, and an open lower end;
    a cut out disposed on a bottom end of the curved side wall of the second end of the housing;
    wherein the cut out is arcuate in shape and extends entirely across the bottom end of the sidewall of the second end of the housing;
    a flap disposed on a side portion of the curved side wall of the housing;
    the flap movable between an open configuration and a closed configuration;
    the flap in operable connection with the open lower end of the housing, such that a flap opening is connected to an opening formed by the open lower end;

a fastener operable connected to the flap and the housing;
at least one air vent disposed on an upper end of the housing.

11. The vaporizer containment tent of claim 10, wherein the cut out is arcuate in shape.

12. The vaporizer containment tent of claim 10, wherein the pair of rigid members define a pair of side walls that are semicircular in shape.

13. The vaporizer containment tent of claim 10, wherein the housing is composed of a rubberized fabric material.

14. The vaporizer containment tent of claim 10, wherein the housing is composed of a vinyl material.

15. The vaporizer containment tent of claim 10, wherein the fastener is a hook and loop fastener.

16. A vaporizer containment tent, comprising:
a pair of semicircular inverted U-shaped side walls defining a hemicylindrical housing therebetween;
the hemicylindrical housing defining a first inverted U-shaped side wall at a first end opposite of a second inverted U-shaped side wall at a second end and an open lower end extending across the entire rectangular area defined by the hemicylindrical housing;
the hemicylindrical housing defining an arcuate cut out at the second end thereof;
the arcuate cut out extending entirely across the second inverted U-shaped side wall of the hemicylindrical housing;
the housing composed of a non-absorbent material;
a three-sided flap disposed centrally on a side portion of the hemicylindrical housing between the first inverted U-shaped side wall and the second inverted U-shaped side wall;
the three-sided flap in operable connection with the open lower end of the housing;
a fastener complementarily disposed on both the side portion of the hemicylindrical housing and a bottom end of the three-sided flap;
a pair of vents, wherein each vent is disposed proximally to each of the first end and the second end of the hemicylindrical housing.

17. The vaporizer containment tent of claim 16, wherein the hemicylindrical housing is made of a rubberized fabric material.

18. The vaporizer containment tent of claim 16, wherein the hemicylindrical housing is made of a vinyl material.

19. The vaporizer containment tent of claim 16, wherein the fastener is a hook and loop fastener.

* * * * *